United States Patent [19]
Barr

[11] Patent Number: 5,226,066
[45] Date of Patent: Jul. 6, 1993

[54] APPARATUS AND METHODS FOR CARDIAC BIPLANE ACQUISITION

[75] Inventor: David A. Barr, San Jose, Calif.

[73] Assignee: Adac Laboratories, Milpitas, Calif.

[21] Appl. No.: 752,159

[22] Filed: Aug. 29, 1991

[51] Int. Cl.$^5$ .............................................. H05G 1/64
[52] U.S. Cl. ...................................... 378/99; 358/111
[58] Field of Search ............................ 378/99; 358/111

[56] References Cited

U.S. PATENT DOCUMENTS

| | | | |
|---|---|---|---|
| 4,204,225 | 5/1980 | Mistretta | 358/111 |
| 4,204,226 | 5/1980 | Mistretta | 358/111 |
| 4,382,184 | 5/1983 | Wernikoff | 378/99 |
| 4,444,196 | 4/1984 | Stein | 358/111 |
| 4,636,850 | 1/1987 | Stewart | 378/99 |
| 4,761,803 | 8/1988 | Oppelt | 358/111 |

OTHER PUBLICATIONS

Siebert, et al., *Interlaced versus progressive readout of television cameras for digital radiographic acquisitions,* Med. Phys. 11(5) Sep./Oct. 1984, pp. 703–707.
*Digital Coronary Angiography,* Cardio, Mar. 1986.
*Advantx Cardiovascular Imaging Systems* brochure and product data, GE Medical Systems.
Pearce, et al., *Digital angiography endures despite inauspicious start,* Diagnostic Imaging, Nov. 1986.

Primary Examiner—Craig E. Church
Attorney, Agent, or Firm—Townsend and Townsend

[57] ABSTRACT

An angiography system is described for acquiring both cine-film and T.V. or digital video images for at least two planes, including at a rate of 30 fps per plane. In one embodiment of the present invention, a single-channel digital acquisition system comprises a frontal x-ray source with corresponding frontal T.V. and frontal cine-film cameras, a lateral x-ray source with corresponding lateral T.V. and cine-film cameras, and circuitry for eliminating motion artifacts.

5 Claims, 10 Drawing Sheets

APPARATUS AND METHODS FOR CARDIAC BIPLANE ACQUISITION

BACKGROUND OF THE INVENTION

The present invention relates generally to the field of radiography and, more particularly, systems for generating cardiac angiograms.

Radiologic examination forms an integral and essential part of evaluating cardiac disease. A radiograph or radiogram is a film or other record produced by the action of actinic rays, typically x-rays, on a sensitized surface. The shadow of the heart, as seen on a standard or "plain" radiograph or by fluoroscopy, is useful for evaluating gross disease processes, such as chamber enlargement. Such studies, however, only demonstrate the outer borders of the heart and great vessels. Considerably more information is obtained when the blood is opacified by injecting a contrast medium into the vascular system, so that the inner borders of the cardiac chambers and vessels can be visualized.

Of particular interest to the present invention is the imaging and diagnosis of coronary artery disease, especially that induced by atherosclerosis. Until recently, the diagnosis of coronary artery disease depended primarily on the ability of a physician to interpret the significance of chest pain described by patients. Objective confirmation required the recognition of transient or persistent electrocardiographic changes, which usually indicated the presence of myocardial ischemia, necrosis, or other secondary myocardial change.

Selective cine coronary angiography, a specialized radiographic technique, provides a useful clinical approach to the precise demonstration of morphologic changes in the human coronary artery vasculature. Under local anesthesia, a catheter is percutaneously introduced, typically in the brachial or femoral artery, and passed retrograde directly into the ascending aorta. The catheter tip is then introduced directly into each of the two coronary orifices. Multiple small doses of contrast medium are injected directly into the orifice of each coronary artery, with the patient typically positioned in different projections.

In a conventional coronary angiography study, x-rays are admitted toward a subject while contrast medium passes through the branches of the coronary tree. Some of the x-rays are absorbed or scattered, while others pass through the subject toward an image intensifier. Upon reaching the image intensifier, the passed-through x-rays are converted to form an optical image which, through the use of mirrors and/or beam splitters, may be focused at either or both a film camera (i.e., 35 mm motion-picture or cine camera) and a T.V. or video camera. In particular, the film camera is used for capturing multiple images as individual photographs. The T.V. camera, on the other hand, is used for capturing multiple images as analog or digital video frames (hereinafter collectively referred to as digital images), which may be acquired, stored, processed and combined to form dynamic video image sequences.

For a typical coronary angiographic exam, approximately ten sequences of images of the heart are obtained. Since the heart and its vasculature are three-dimensional in structure, several projections (i.e., different perspectives) are often obtained. A single sequence typically lasts approximately eight seconds and comprises a plurality of frames captured at a frame rate of about 7.5 to 60 frames per second (fps); sometimes, rates as high as 90 fps or 150 fps are used.

Since excess irradiation is undesirable, the x-rays are emitted in a pulsed fashion, at the lowest possible exposure level. Typically, each frame within a sequence is formed by transmitting an x-ray pulse of about 20–100 micro-Roentgens over a period of 2–10 milliseconds. In a technique similar to flash or strobe photography, the cine camera and T.V. camera capture the pulses while operating at slower shutter speeds (i.e., longer durations than the x-ray pulse) so that none of the x-rays are wasted. In contrast to other body tissues, the actively contracting heart requires shorter pulses and more frames to capture a focused, non-blurred image sequence.

It would be desirable to provide a cardiac acquisition system which includes the ability to acquire both cine-film and digital images simultaneously from two planes, e.g., from frontal and lateral perspectives. These "biplane" studies should include studies acquired at 30 fps or more for each plane. To reduce scatter (i.e., stray x-rays from the other plane), each plane should be acquired at a different time (out of phase) relative to the other plane. Furthermore, the system should operate with only a single digital image acquisition processor, thereby reducing costs. The present invention fulfills this and other needs.

SUMMARY OF THE INVENTION

An angiography system is described for providing both cine-film and T.V. images for at least two planes, including a rate of 30 fps per plane. In one embodiment of the present invention, a single-channel biplane acquisition system includes a computer system, an interface, and an x-ray imaging system. In operation, x-ray images are obtained from the imaging system and are supplied to the computer system through the interface.

The imaging system includes a frontal imaging subsystem having a frontal x-ray source with corresponding frontal T.V. and frontal cine-film cameras, and includes a lateral imaging subsystem having a lateral x-ray source with corresponding lateral T.V. and cine-film cameras; circuitry is provided for eliminating motion artifacts.

In a preferred embodiment, the circuitry for eliminating motion artifacts includes a timing delay which brings the lateral or second video signal into phase synchronization with the frontal or first video signal. In a preferred embodiment, a 30 fps acquisition rate (about 33 millisecond frame period) is employed for both the frontal and lateral planes, with the lateral system 180 degrees out of phase relative to the frontal system, representing a shift of about 16.67 milliseconds. In a preferred embodiment, a video delay unit allows the vertical retrace periods of the lateral TV scan to be shifted to where the lateral x-ray pulses occur, thus correcting the Vertical Retrace Pulsing (VRP) of the lateral T.V. scan to match that employed on the frontal scan. The delayed signal of the lateral scan is then supplied to a multiplexor which may then supply the single-channel acquisition system with a video signal multiplexed between two synchronized video sources.

DESCRIPTION OF THE PREFERRED EMBODIMENTS

Conventional biplane cine-film acquisition (30 fpb per plane)

Figure 1A:
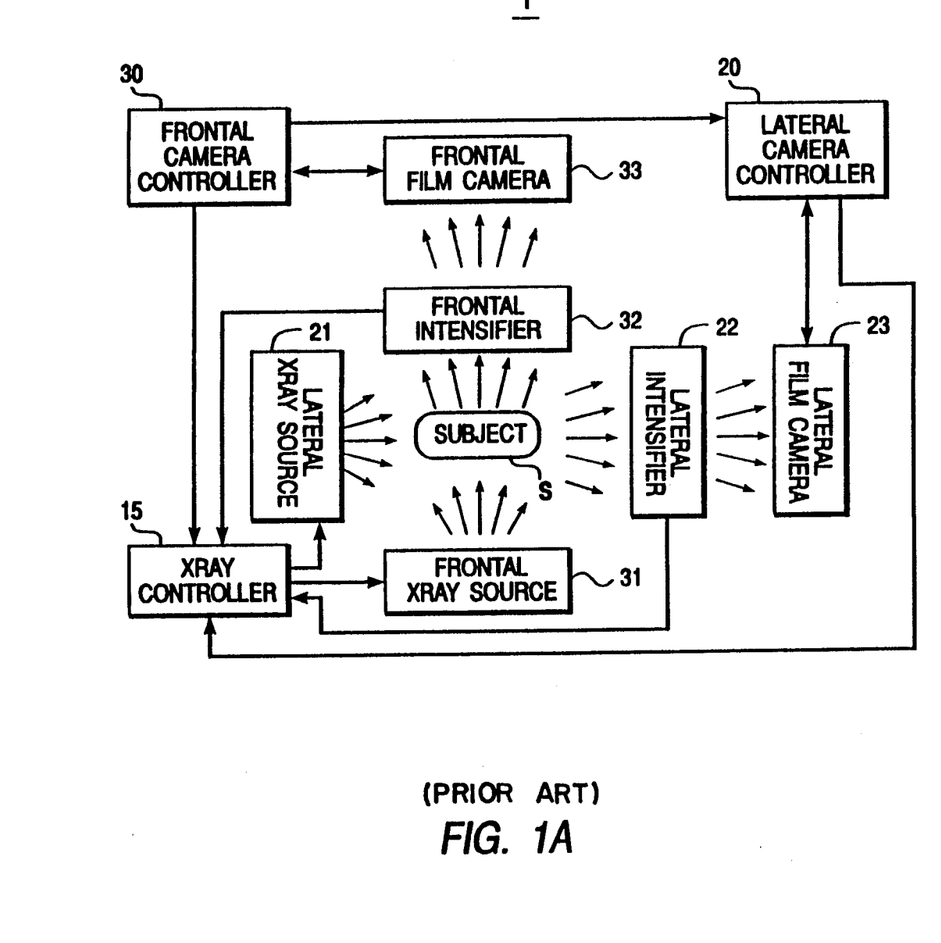
FIG. 1A is a block diagram of a biplane cardiac cineangiography system.
Figure 1B:
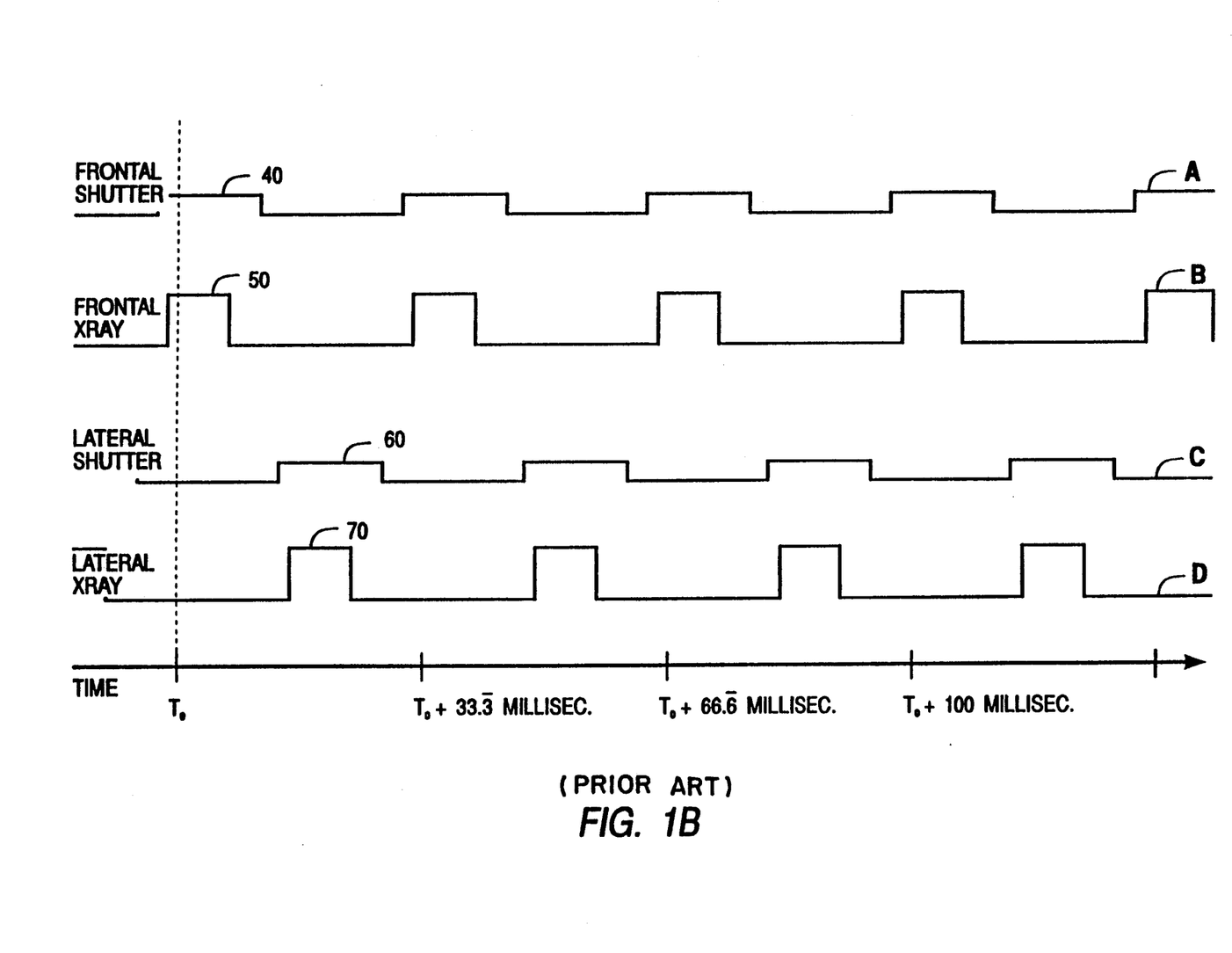
FIG. 1B is a timing diagram for the system of FIG. 1A, operating at 30 fps.

Referring now to FIGS. 1A–B, a conventional biplane cine-film acquisition system, operating at 30 fps per plane, is illustrated. Angiographic acquisition system 1 includes an x-ray controller 15, a frontal x-ray source 31, a frontal intensifier 32, a frontal film camera 33, and a frontal camera controller 30. In addition, system 1 includes a lateral x-ray source 21, a lateral intensifier 22, a lateral film camera 23, and a lateral camera controller 20. During cardiac cineangiography, the system 1 provides cine-film images from two planes, such as frontal and lateral views.

The operation of the system 1 at 30 fps (frames per second) is as follows. While injecting a bolus of contrast media into the coronary vessel of interest, a cardiologist activates the frontal camera controller 30 (e.g., with a foot-controlled switch). The frontal film camera 33, under the control of the frontal camera controller 30, exposes cine-film at a rate of 30 fps. The operation of the frontal film camera 33 resembles that of a conventional movie camera. Specifically, when each frame of cine-film is advanced into position a shutter of the camera momentarily opens to admit an image from the frontal intensifier 32, thus exposing the frame of film. As shown by tracing A, the frontal shutter opens momentarily at a frequency of 30 Hertz, represented by wave 40 of tracing A.

In a fashion similar to strobe-synchronized photography, the frontal x-ray source 31 is synchronized to the frontal film camera 33 as follows. During the period of time that the frontal shutter is opened (wave 40 of A), a shutter open signal is sent from the frontal camera 33 to the frontal camera controller 30. The frontal shutter signal (or a related signal) is then sent from the controller 30 to the x-ray controller 15 and to the lateral camera controller 20.

Under the control of x-ray controller 15 and in response to the frontal shutter signal, the frontal x-ray source 31 emits an x-ray pulse towards the subject S. As shown by the wave 50 of tracing B, the frontal x-ray fires at a rate of 30 Hertz, i.e., 30 x-ray pps (pulses per second). From the emitted x-rays which pass through the subject S, an image is formed on the frontal intensifier 32, which typically includes a phosphorous screen or the like. Completing this imaging loop, the image at frontal intensifier 32 is recorded on the current frame of cine-film being exposed by the frontal film camera 33.

The exposure of the second or lateral plane occurs as follows. As described above, the frontal shutter signal is sent to the lateral camera controller 20, thus the lateral controller 20 may be "slaved" (at any chosen or predetermined relative phase) to the frontal camera controller, and hence the frontal film camera 33. To minimize scatter between the two planes, the lateral exposures and x-ray pulses occur out of phase from the frontal pulses, thereby allowing each shutter to reject scatter from the opposite plane. Commonly, the lateral exposures occur 180 degrees out of phase. Thus for the frontal x-ray source delivering 30 pps, the lateral exposures and pulses are about 17 milliseconds out of phase.

Referring to tracings C and D of FIG. 1B, this alternating pulse sequence is illustrated for system 1 where the two planes are acquired 180 degrees out of phase. Under the control of lateral camera controller 20 (which has been slaved to the frontal camera controller 30), the lateral film camera 23 exposes cine-film at a rate of 30 fps. The operation of lateral film camera 23 is similar to that of frontal film camera 33. Specifically, with each frame of film advanced into position, the shutter of the camera opens momentarily. While the shutter is opened, a lateral shutter open signal, such as the wave 60 of tracing C, is sent from the lateral film camera 23 to the lateral camera controller 20; this signal is then sent to the x-ray controller 15.

Under control of the x-ray controller 15 and in response to the lateral shutter signal, the lateral x-ray source 21 emits x-ray pulses towards the subject S. Indicated by tracing D, these pulses occur at a frequency of 30 pps, such as the wave 70. The emitted x-ray pulses which pass through the subject S strike the lateral intensifier 22 and are recorded by the exposed film of the lateral film camera 23. Thus, the two planes, operating 180 degrees out of phase, obtain cine images at 30 fps per plane, with the exposures occurring alternately on the two planes. While T.V. cameras may operate in this mode, single-channel digital biplane acquisition is not provided by prior art systems.

Conventional Biplane Digital Acquisition (15 ips per Plane)

Figure 2A:
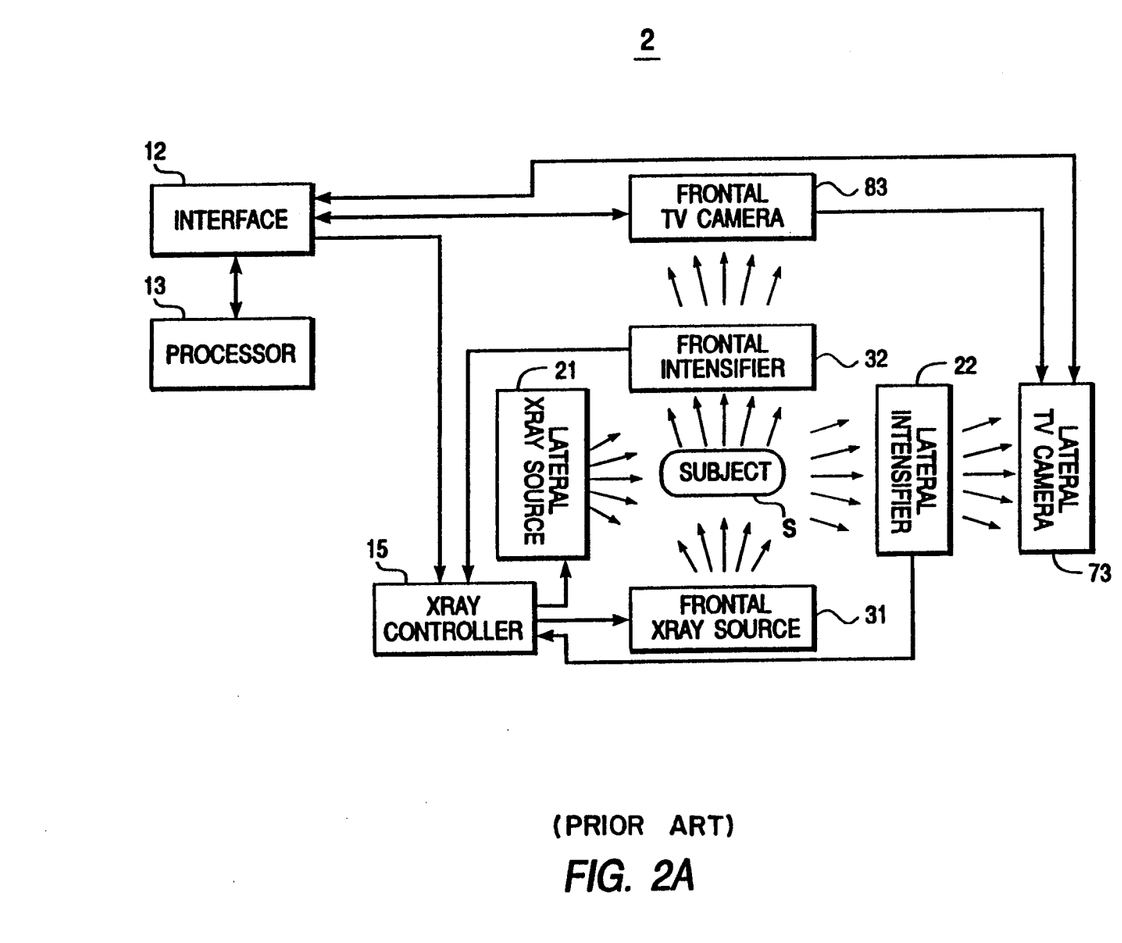
FIG. 2A is a block diagram of a single-channel biplane digital video acquisition system.
Figure 2B:
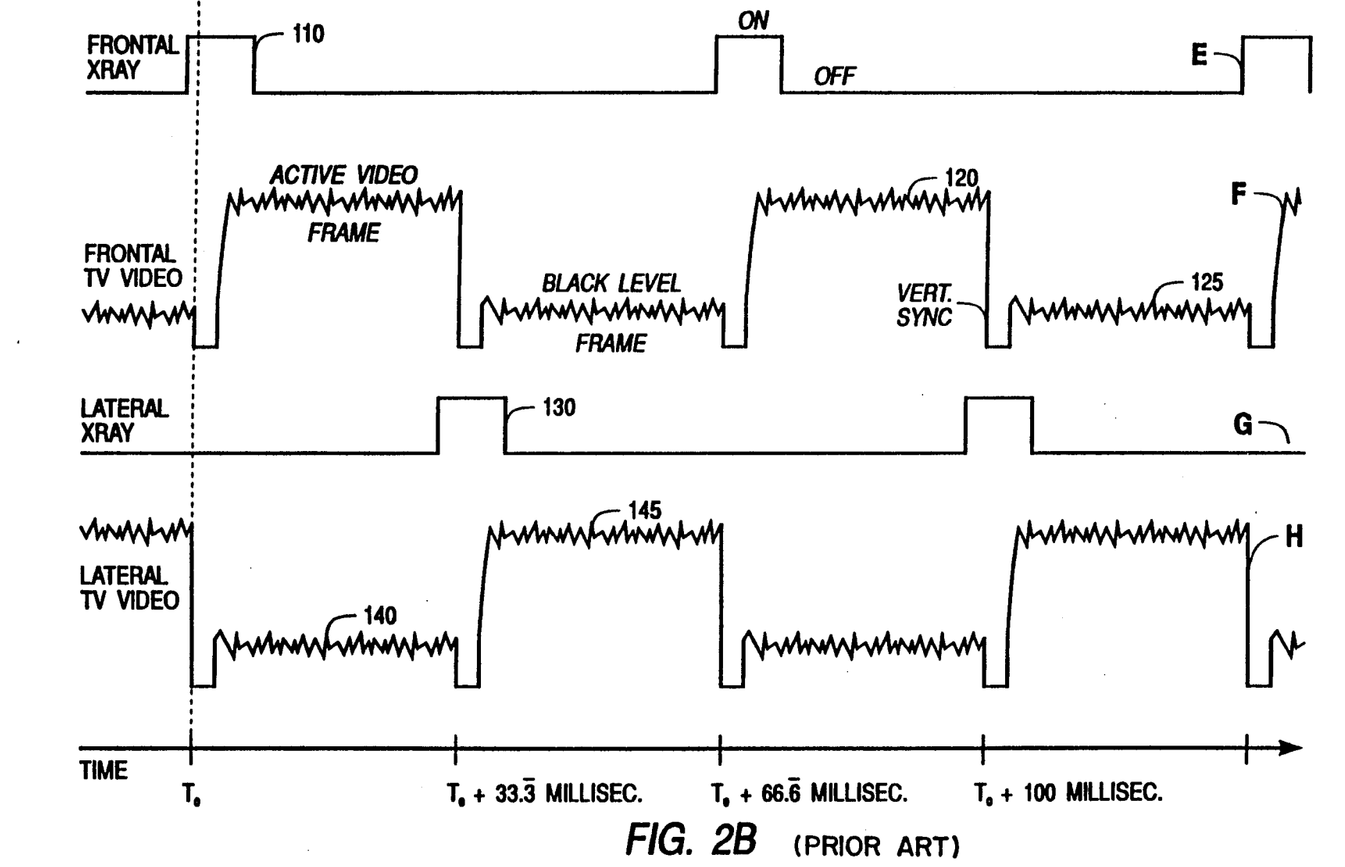
FIG. 2B is a timing diagram for the system of FIG. 2A, operating at 15 ips per plane.

Referring now to FIGS. 2A–B, a single-channel digital (video) biplane acquisition system 2 will be described. The system 2 is similar to system 1, except that digital video images are obtained instead of cine-film images. Digital video acquisition, processing, and display of coronary angiograms provides certain improvements over conventional cine-film acquisition. In particular, the digital images are more convenient since they are immediately available for review by the cardiologist without waiting for the film images to be chemically developed. Furthermore, the digital images can be quickly enhanced, magnified, and processed by computer programmed quantitative analysis before display. Digital images also benefit from general digital techniques, such as rapid telecommunication transfer (e.g., via modem) and archival storage without image degradation. For a general review of digital acquisition, see, Digital Coronary Angiography, CARDIO, Mar. 1986.

The system 2 comprises a single-channel acquisition processor 13, an interface 12, an x-ray controller 15, a frontal x-ray source 31, a frontal intensifier 32, and a frontal T.V. camera 83. In addition, the system 2 includes a lateral x-ray source 12, a lateral intensifier 22, and a lateral T.V. camera 73.

With particular reference to the timing diagrams of FIG. 2B, the operation of system 2 will be described. During coronary angiography, as the cardiologist is injecting a bolus of contrast media, the interface 12 is simultaneously activated. Under control of the interface 12, the x-ray controller 15 triggers the frontal x-rays source 31, with x-ray pulses emitted at 15 pps, such as the wave 110 of tracing E. Emitted x-ray pulses which pass through the subject S strike the frontal intensifier 32, thus forming a visual image which may be recorded by a camera or similar means.

Also under the control of interface 12 and synchronized with the frontal x-ray pulses, the frontal T.V. or video camera 83 records the images at the frontal intensifier 32 as active video frames, such as the frame 120 of tracing F. Since the single-channel acquisition processor 13 can only acquire a single video signal (typically 30 video frames or images per second (ips)), it can acquire biplane images from cameras 83, 73 by alternately acquiring video frames from each plane (typically 15 ips per plane). Since the two video signals are phase synchronized, the system 2 can alternatively acquire images from both planes by multiplexing between the two video signals. A multiplexor (MUX) switches between the two video signals during the vertical retrace periods (VERT. Sync) of each signal. The VERT. Sync periods of each video signal occur simultaneously since the signals are phase synchronized. Each video signal F, which operates at 30 ips, also includes black level frames, such as frame 125, between the active video frames.

The T.V. cameras 73, 83 are synchronized via "slave sync" signal generated by the frontal T.V. camera 83 and transmitted to the lateral T.V. camera 73. The slave sync signal establishes the frequency and phase at which the lateral (or slave) T.V. camera 73 should operate. The frontal (or master) T.V. camera 83 generates the slave sync signal such that the lateral T.V. camera 73 operates at the same phase as the frontal T.V. camera 83.

Referring to tracings G and H, acquisition of the lateral plane will be described. Under control of the interface 12, the x-ray controller 15 causes the lateral x-ray source 21 to emit an x-ray pulse, such as the wave 130 of tracing G, at a rate of 15 pps. Upon firing of the lateral x-ray source 21, the emitted x-rays which pass through the subject s strike the lateral intensifier 22 and form a visible image which may be recorded with a camera. Typically this will be synchronized out of phase so that the x-ray pulse 130 occurs approximately coincident with the vertical retrace period, immediately following the black level frame 140 and preceding the active video frame 145.

Also under the control of interface 12, the lateral T.V. camera 73 records the image formed at the lateral intensifier 22 by the x-ray pulse 130. Like the frontal system, the lateral T.V. video, represented by tracing H, comprises active video images 145 occurring at 15 ips, with black level frames 140 interposed and thus also occurring at 15 ips. The black level frames 140 for one plane occur during the active video frames from the other (e.g., frontal) plane, thereby allowing the multiplexor to skip over black level frames such as frames 125, 140 and instead select only active video frames such as frames 120, 145 for digital acquisition.

During cardiac cineangiography examination, it is desirable to acquire digital images from both the frontal and lateral T.V. cameras while simultaneously recording 35 mm cine-film on both imaging chains. In particular, it is desirable that at least the two cine cameras operate at 30 fps, especially if this can be implemented as a single-channel digital biplane acquisition system (as opposed to two single-channel acquisition systems operating simultaneously, one for each plane).

One approach to reducing equipment costs is to implement a single-channel digital biplane acquisition system which acquires digital images alternately from each plane at only one-half the single-plane rate (typically 15 ips per plane). With this approach, however, the cine-film cameras also operate at that rate (i.e., 15 fps per plane) to maintain compatibility between the pulsing sequences required for both the digital and cine-film cameras.

Figure 3:
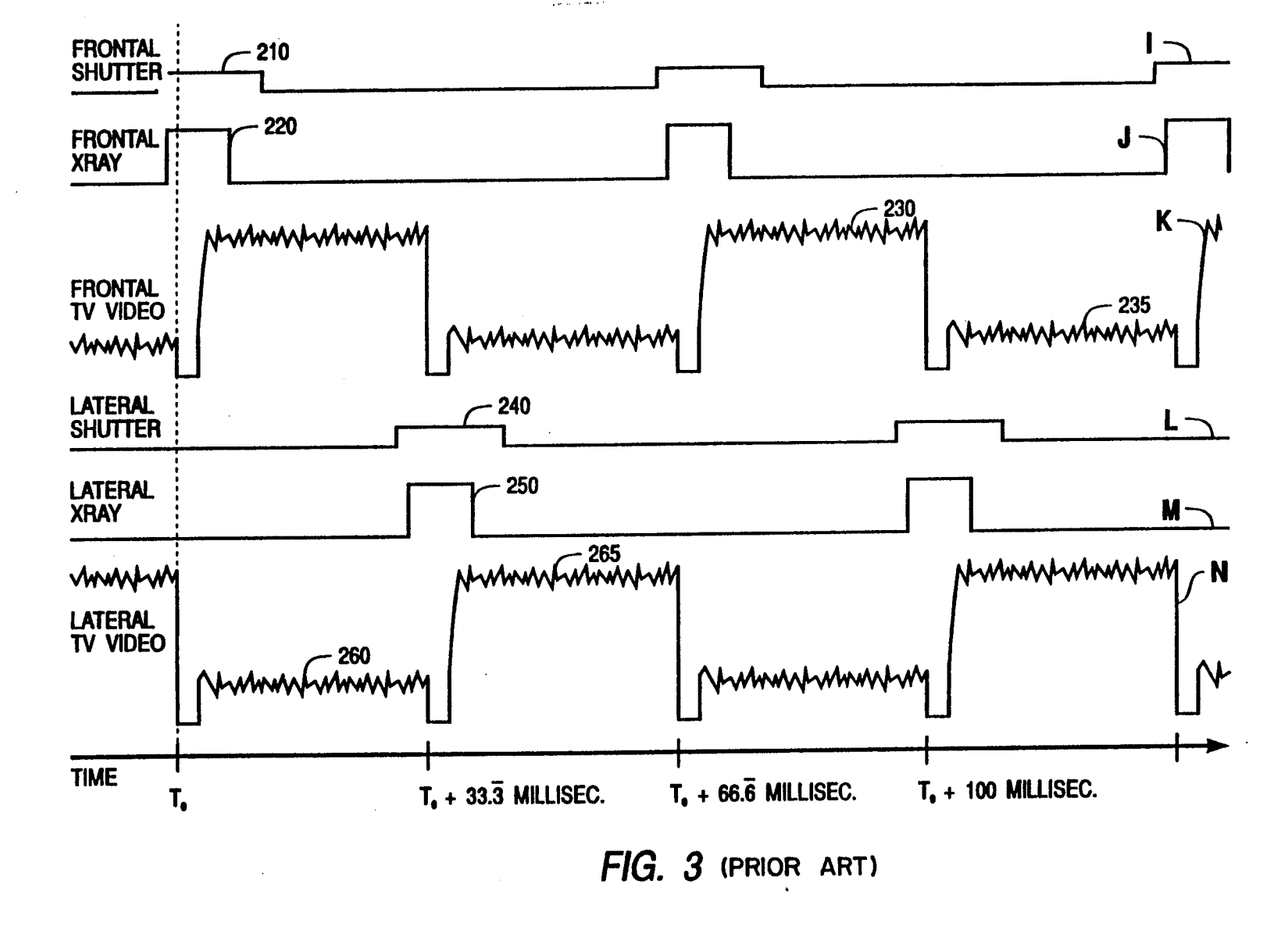
FIG. 3 is a timing diagram for single-channel cardiac digital and cine-film biplane acquisition at 15 fps per plane.

Referring to FIG. 3, the operation of such a system, i.e., both digital and cine-film biplane acquisition, is shown. The operation of the frontal system is shown by tracings I-K. A frontal shutter open signal, such as wave 210 of tracing I, triggers a frontal x-ray pulse, such as the wave 220 of tracing J. The frontal T.V. video camera records the resulting image as an active video image or frame, such as the image frame 230 of tracing K. Black level images or frames 235 are interposed between the active video frames (as described hereinabove) since the TV camera typically operates at 30 video frames per second even though the x-ray exposures occur at only 15 pps.

With reference to tracings L-N, acquisition of the lateral image will be described. Out of phase from the frontal x-ray system, such as 180 degrees, the lateral shutter opens, indicated by wave 240 of tracing L. In response, this triggers a lateral x-ray pulse, such as the wave 250 of tracing M. Also, the lateral T.V. video camera records the image which appears at the lateral image intensifier as an active video image 265, which occurs in response to the x-ray pulse 250. As with the frontal system, the lateral T.V. video tracing includes black level video images 260 interposed between the active video images 265.

While the foregoing system allows both digital and cine-film images to be obtained from two planes, the maximum rate obtained is only 15 ips, and thus has several disadvantages. In particular, a 15 pps rate is too slow for most clinical applications. One problem is the annoying flicker of images which may be perceived when the frame rate is less than 30. Another problem is the loss of valuable clinical information which occurs at such a slow frame rate. In clinical practice, most practitioners prefer to acquire diagnostic images of at least 30 fps, with both digital and cine-film images obtained from two planes, therefore, another approach must be employed.

Figure 4:
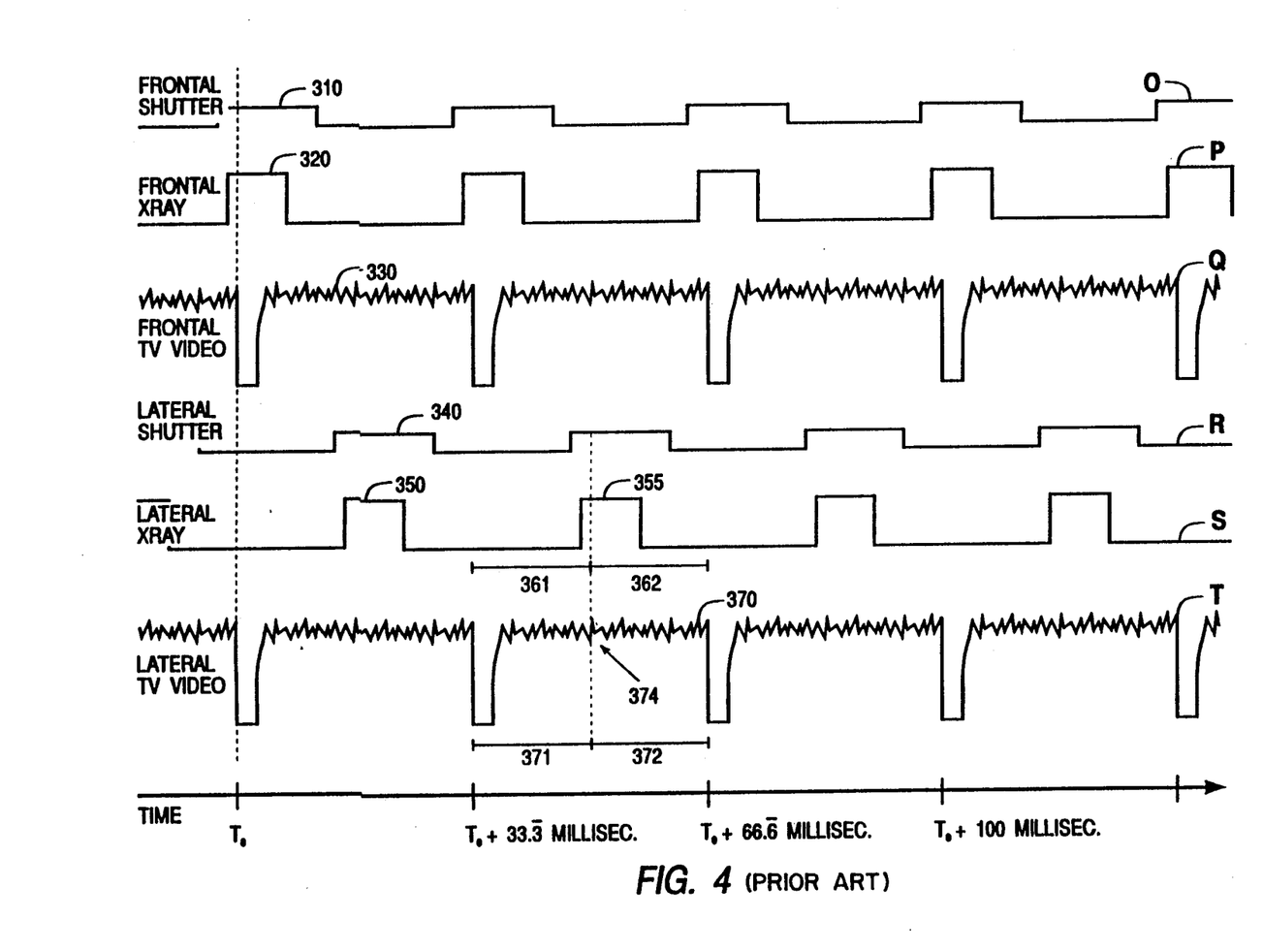
FIG. 4 is a timing diagram for single-channel cardiac digital and cine-film biplane acquisition at 30 fps per plane.

Referring now to FIG. 4, the operation of a single-channel biplane acquisition system is shown. Tracings O and P are timing diagrams for the frontal shutter and frontal x-ray pulses, respectively. Similar in operation to tracings B of system 1, the frontal shutter signal and frontal x-ray source are synchronized in operation. For each frontal shutter signal, such as the wave 310 of tracing O, there is a corresponding frontal x-ray pulse, such as the wave 20 of tracing P. Since the frontal system operates at a frequency of 30 Hertz, thirty shutter signal/x-ray pulse pairs occur each second for the frontal plane.

As shown by tracing Q, the frontal T.V. video is synchronized such that a vertical retrace (vertical sync) occurs approximately coincidental with each x-ray pulse 320. In this manner, the frontal imaging system provides 30 fps of cine-film and 30 ips of TV camera video representing images from a frontal x-ray source firing at 30 pps.

Referring to tracings R and S, the corresponding lateral cine-film acquisition is again acquired out of phase, typically 180 degrees, to allow the lateral cine camera shutter to reject scatter from the frontal x-ray source. As shown in tracing R, the lateral shutter opens (wave 340) at 30 fps, thus triggering a lateral x-ray pulse (wave 350 of tracing S). A lateral TV video signal (tracing T) occurs in response to the x-ray exposures at the lateral image intensifier. The vertical retrace of the lateral TV video signal, however, does not occur approximately coincident with the lateral shutter or the lateral x-ray pulses. The synchronization of the lateral T.V. video signal is as follows. Lateral video tracing T comprises a plurality of active video images or frames 370 which are synchronized to the frontal T.V. video (tracing Q), not the lateral x-ray source (tracing S). To alternately acquire both frontal and lateral video signals, a single-channel system requires that the video signals be in phase synchronization (i.e., the vertical sync signals must not be out of phase between the two tracings). In particular, a single-channel digital biplane acquisition system can only multiplex phase-synchronized video signals; otherwise, one frame would require processing before another frame had been processed. Synchronizing the lateral T.V. video signal with the frontal T.V. video signal, however, creates a serious "motion artifact" which is caused by a new lateral x-ray exposure occurring midway through the readout of the lateral T.V. image (from the lateral image intensifier).

Figure 5A:
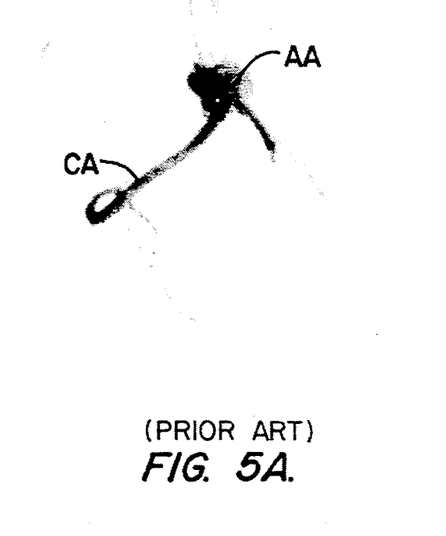
FIGS. 5A–D are digital angiograms illustrating the motion artifacts of the acquisition of FIG. 4.
Figure 5B:
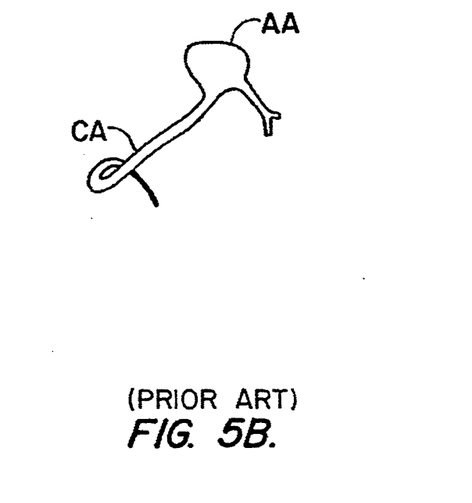
Figure 5C:
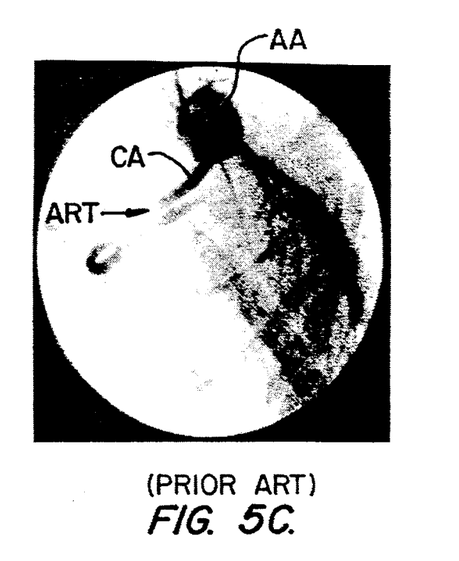
Figure 5D:
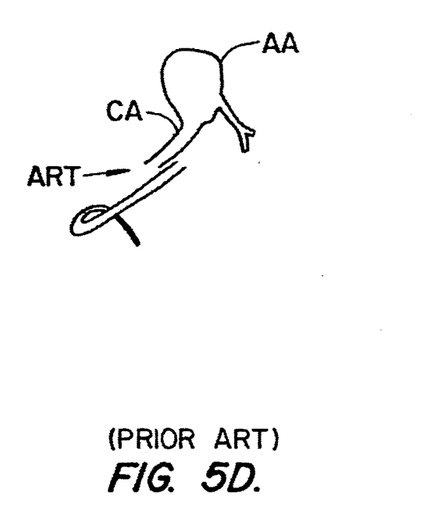

Referring now to FIGS. 5A–D, this artifact is illustrated. In FIG. 5A (shown stylized in FIG. 5B), a digital frame is shown where the coronary artery CA is correctly visualized. The ascending aorta AA is also imaged (as a result of back wash of injected contrast media). In FIG. 5C (shown stylized in FIG. 5D), however, the coronary artery CA, previously shown as a uniform Or continuous structure, is now imaged with the incorrect pulse phasing as two discontinuous vessels. Thus, an artifact Art has been introduced into the frame as a result of the motion of the vessel. These artifacts can interfere substantially with the diagnostic analysis. Worse yet, subtle artifacts may even be misdiagnosed as vascular lesions, with the patient receiving inappropriate treatment accordingly.

Referring again to tracings R-T of FIG. 4, the source of the motion artifact is shown with reference to a single video image frame 370. Since the lateral video tracing T is phase synchronized with the frontal T.V. video (tracing Q), its vertical retrace periods are not synchronized with x-ray pulses from the lateral x-ray source S. Hence, each lateral video image derives its information from two x-ray pulses and hence from two separate images at the image intensifier. The first half 371 of video frame 370 derives its image from x-ray pulse 350 and the second half 372 derives from x-ray pulse 355. Therefore, roughly midway through the lateral TV readout of frame 370, a new x-ray pulse 355 occurs, and the lateral image intensifier updates the TV camera, which then reads out the image from this new pulse.

As a result of this synchronizing incompatibility, each lateral x-ray pulse occurs roughly in the middle of the T.V. frame scan from the lateral T.V. camera. If the subject is moving, such as a rapidly beating heart, the TV camera is updated with an image which has in fact changed. Even if the subject itself were stationary, there would likely be a discrepancy from the top half to the bottom half of each lateral frame since the injected contrast media is rapidly moving through the patient's vessels.

Single-Channel Biplane Acquisition System

Figure 6:
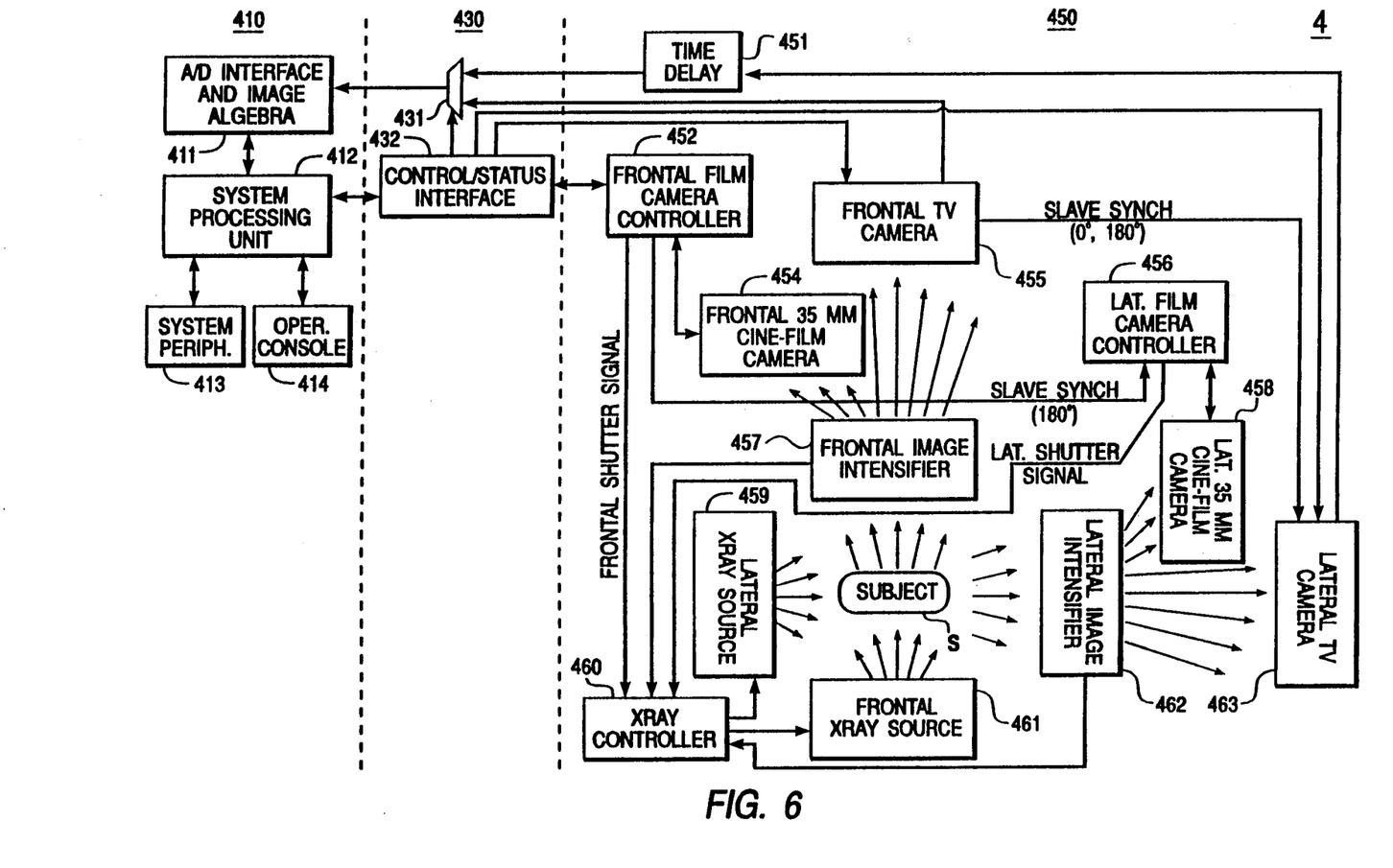
FIG. 6 is a block diagram of a digital and cine-film biplane acquisition system of the present invention.

Referring now to FIG. 6, a biplane cardiac angiography system of the present invention is illustrated. Biplane cine and single-channel digital biplane acquisition system 4 includes a computer system 410, an interface 430, and an x-ray imaging system 450. In general, x-ray images are obtained from imaging system 450 and are supplied to computer system 410 through interface 430.

The x-ray imaging system 450 functions to obtain biplane cine and video images. System 450 includes a frontal imaging subsystem comprising film camera controller 452, a frontal 35 mm cine-film camera 454, a frontal image intensifier 457, a frontal TV camera 455, a frontal x-ray source 461, and an x-ray controller 460. In addition, imaging system 450 includes a lateral imaging subsystem comprising film camera controller 456, a lateral 35 mm cine-film camera 458, a lateral T.V. camera 463, a lateral image intensifier 462, and a lateral x-ray source 459.

In one embodiment, a Siemens BICOR system (available from Siemens Aktiengesellschaft of Erlangen, Germany) forms the imaging system 450 components 452, 454, 456–462, while an ADAC DTV-4114 T.V. camera (available from ADAC Laboratories of Milpitas, Calif.) forms the T.V. cameras 455 and 463. Other imaging systems, such as General Electric's Advantx Cardiovascular imaging systems (available from General Electric of Milwaukee, Wis.), are known and may be likewise employed.

According to the present invention, system 450 is provided with circuitry for eliminating artifacts. In particular, system 450 includes, in addition to frontal and lateral imaging subsystems, a time delay circuitry 451 (described hereinbelow) for eliminating motion artifacts in the lateral (or frontal) imaging subsystem.

Computer system 410 functions to control the operation of imaging system 450 and to acquire and process digital images. Computer system 410 includes an A/D interface and image algebra circuit 411, a system processing unit 412, system peripherals 413, and an operator console 414. System processing unit 412, which is coupled to operator console 414, controls certain aspects of the operation of system 4 via interface 430. In particular, operator commands are entered through the operator console 414 for processing by system processing unit 412; the operator console 414 includes a plasma touch screen, an alphanumeric keyboard, a remote infrared control keypad and a CRT display. In one embodiment, the system processing unit 412 includes a DEC LSI 11-73 central processing unit with 1 megabyte of CPU memory, a 22-bit Q-bus, and a 64-bit digital video bus.

System processing unit 412 also processes digital images from circuit 411. In particular, the A/D interface and image algebra circuitry 411 includes analog-to-digital circuits for converting analog video signals received from the imaging system 450 (through interface 430) into digital video signals. The digital signals can be optionally processed by a 32-bit floating point processor interfaced to a video bus. The resulting video image data is then stored in a video memory. System processing unit 412 is also connected to system peripherals 413 which may include a printer for generating still photographs of a video image stored in memory.

Interface 430 provides a communication link between the computer system 410 and the x-ray imaging system 450. The interface 430 includes a control/status interface 432 and a video multiplexor 431. Control/status interface 432 is connected directly to the frontal and lateral T.V. cameras 455, 463 and the frontal film camera controller 452, thus enabling the system 4 to perform biplane cardiac angiography. Under control of the system processing unit 412, the control/status interface 432 generates signals for controlling both T.V. cameras 455, 463 and both cine-film cameras 454, 458 (through frontal film camera controller 452). Frontal and lateral camera controllers 452, 456 are conventional camera controllers (e.g., Siemens BICOR system) which have been slightly modified. In particular, the controllers have been modified to enable the control/status interface 432 to establish the frequency and phase of operation of the frontal and lateral cine-film cameras 454, 458 via control signals supplied to the frontal film camera controller 452. The frequency and phase at which the frontal and lateral cine film cameras 454, 458 may operate are described hereinbelow.

Each of the television cameras 455, 463 may be an automated 2-piece video camera capable of high resolution imaging (e.g., 512×512 or 1024×1024 pixel resolution) over a wide dynamic range (e.g., approximately 1000:1). Each camera, which may be an ADAC DTV-4114 T.V. camera, operates at selectable scanning speeds, including slow (7.5 fps), standard (30 fps), and fast (60 fps). Cameras 455, 463 receive a scan speed select signal from the system processor 412, as derived from operator inputs. Each camera accumulates at a target surface the image produced at image intensifier 457 or intensifier 462 (in response to x-rays). The DTV-4114 T.V. camera includes a vidicon-type image tube scanned by an electron beam to read the image accumulated at the target layer of the vidicon-type tube. The lateral T.V. camera 463 receives a slave sync signal from the frontal T.V. camera 455. The slave sync signal establishes the frequency and phase at which the lateral (or slave) T.V. camera 463 should operate. The frontal (or master) T.V. camera 455 generates the slave sync signal based on inputs provided by the system 410 via interface 430 such that the lateral T.V. camera 463 operates at either a zero or 180 degree phase delay relative to the frontal T.V. camera 455. Any other phase delay (e.g., from zero to 360 degrees) is possible by reconfiguring the frontal T.V. camera to generate the slave sync signal with any desired phase. In another embodiment, a solid-state T.V. camera is used which includes a solid-state image sensor (e.g., array of image cells) for accumulation and readout of photo charge at each respective cell. For a further description of a T.V. camera suitable for use in digital radiographic acquisition, see Seibert et al., *Interface Versus Progressive Readout Of Television Cameras For Digital Radiographic Acquisitions*, Medical Physics 11 (5), Sept./Oct. 1984.

System 4 functions to generate video and film images from biplane x-ray exposures of a subject. A normal operating sequence occurs as follows. An operator, such as a physician, activates the system through a foot-controlled switch (typically while injecting a bolus of contrast media in the vessel of interest). The system processing unit 412 receives this request via the control/status interface 432. In response, the cine cameras 454, 458 begin operation with their frequency and phase specified by the control/status interface 432 via camera controllers 452, 456. Camera 454 makes a series of exposures at the operator pre-selected rate. Synchronization of the remaining components of imaging system 450 depend on the shutter of frontal camera 454. When the shutter of camera 454 is open, a "shutter open" signal is sent back to controller 452. In response, controller 452 sends the frontal shutter signal to x-ray controller 460 which activates frontal x-ray source 461. X-ray source 461 emits an x-ray pulse which passes through the subject S and strikes the image intensifier 457. Corresponding images (from the image intensifier) are recorded on cine-film camera 454 and frontal T.V. camera 455. The foregoing sequence is essentially repeated, out of phase, for the lateral subsystem.

Figure 7:
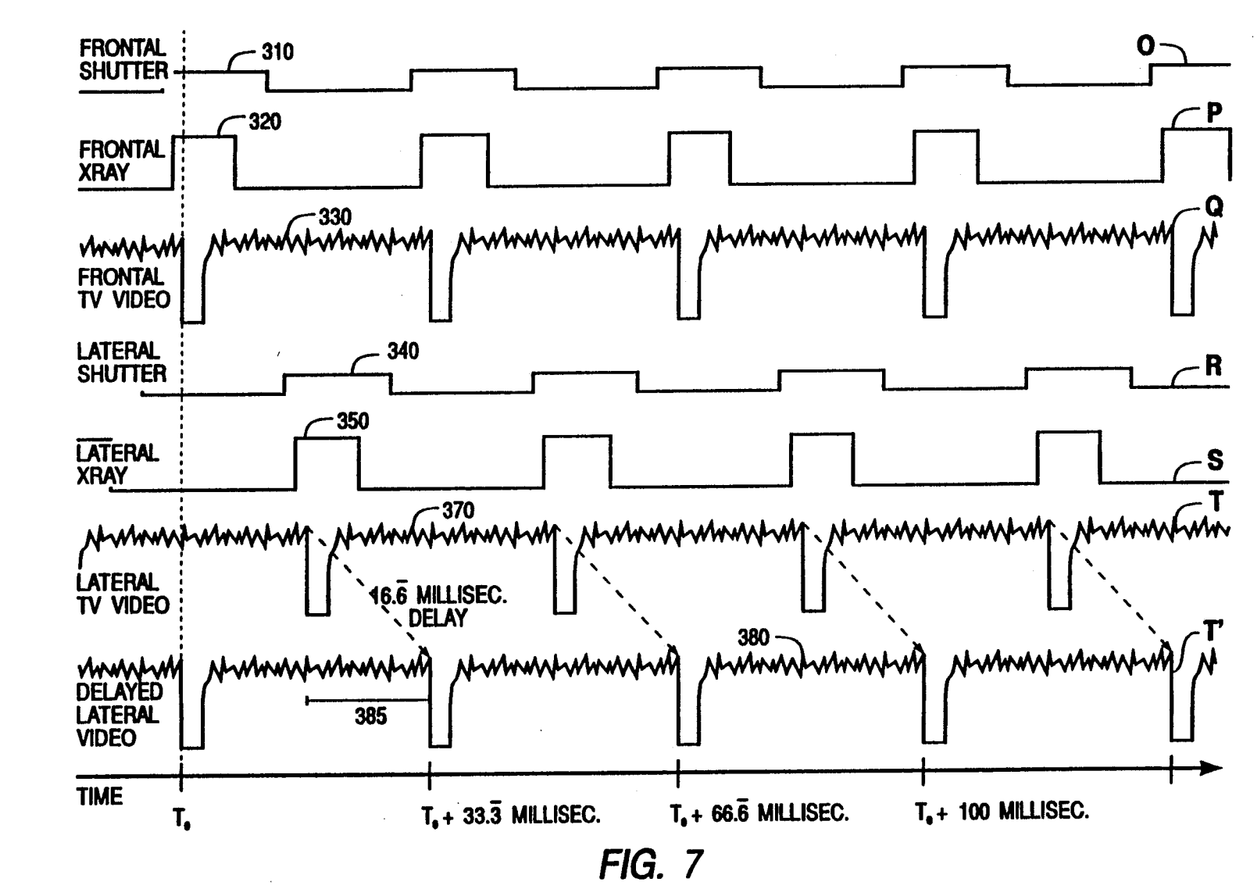
FIG. 7 is a timing diagram for the system of FIG. 6.

Referring now to FIG. 7, the operation of system 4 will be further described with reference to timing diagrams O-T. As shown in tracing O, a series of shutter open signals, such as the wave 310, are transmitted by the frontal cine-film camera 454. Each of the signals is received by the frontal film camera controller 452 and supplied to the x-ray controller 460 as a frontal shutter signal. Under control of the x-ray controller 460, the frontal x-ray source 461 emits x-ray pulses, such as the wave 320 of tracing P. Simultaneously, the frontal T.V. camera 455, which is synchronized through the control/status interface 432, provides a corresponding active video frame, such as the frame 330 of tracing Q. Thus, the frontal shutter (camera 454), frontal x-ray pulse (source 461), and frontal video (camera 455) all operate synchronously at 30 fps.

The lateral x-ray, cine-film, and T.V. video timing are as follows. The lateral film controller 456 receives a slave sync signal from the frontal film camera controller 452. The lateral cine camera controller 456 receives the slave sync signal which establishes the operating frequency and phase for the lateral cine camera 458. The lateral cine camera 458 is typically operated out of phase relative to the frontal cine camera 454 so that each shutter will be closed and reject the scattered x-rays which occur when the opposite plane makes an exposure. In the preferred embodiment, non-zero relative phase differences are used such as about 30 to 180 degrees (180 degrees is most common). Under control of the lateral film camera controller 456, the lateral cine-film camera 458 opens its shutter and asserts a lateral shutter open signal, such as the wave 340 of tracing R. The lateral shutter open signal is received by the lateral controller 456 and is sent to the x-ray controller 460 (alternatively, the signal may be sent directly from the camera 458 to the controller 460). In response to the lateral shutter signal and under the control of x-ray controller 460, the lateral x-ray source 459 emits an x-ray pulse (wave 350 of tracing S) towards the subject for creating an image on the lateral image intensifier 462.

The phase difference of the lateral TV camera 463 relative to the frontal TV camera 455 is set approximately equivalent to the phase difference of the lateral cine camera 458 relative to the frontal cine camera 454. In particular, the lateral x-ray pulses (such as wave 350 of tracing S) occur approximately coincident with the vertical retrace periods of the lateral TV video signal (tracing T). Also, a single active lateral TV image (such as frame 370 of tracing T) arises from a single x-ray pulse (wave 350). Thus, a single lateral x-ray pulse creates an image on the lateral image intensifier 462 which is read by a single lateral T.V. video frame, thereby eliminating the motion artifact that would have arisen by synchronizing the lateral video to the frontal video. At this point, however, the lateral T.V. video is out of phase (e.g., measured by the relation of the vertical sync signals) to the frontal T.V. video, and thus may not be processed by a single-channel acquisition system.

According to the present invention, the lateral T.V. video signals (tracing T) are sent from the lateral T.V. camera 463 to a time delay circuit 451 where they are delayed by a predetermined amount of time. Specifically, the delayed lateral video signal (tracing T') is shifted relative to the frontal T.V. signal so as to bring the two into phase alignment. In a preferred embodiment, a 30 fps (33.3 milliseconds T.V. frame period) is employed with the lateral system 180 degrees out of phase, thus requiring a shift of 16.7 milliseconds. This delay shifts the vertical retrace periods of the lateral video (tracing T') to match those of the frontal video (tracing Q). The lateral video (tracing T') is then supplied to multiplexor 431 which may then supply the single-channel computer 410 with synchronized, multiplexed video signals. The control/status interface 432 instructs the multiplexor 431 to switch between the frontal TV video (tracing Q) and the delayed lateral video (tracing T'), typically during each vertical retrace period, thereby yielding distinct video images alternately from the frontal and lateral subsystems.

Those skilled in the art will appreciate other frame rate/phase angle combinations which may be employed using the teachings of the present invention. By way of illustration and not limitation, frame rates from 7.5 to 60 with phase shift ranging from 0 to 360 degrees (in 45 degree increments) include the following:

TABLE I

| Rate (fps) | Frame (millisec) | Phase (angle) | Shift (millisec) |
|---|---|---|---|
| 7.5 | 133.33 | 0 | 0.00 |
| 7.5 | 133.33 | 45 | 16.67 |
| 7.5 | 133.33 | 90 | 33.33 |
| 7.5 | 133.33 | 180 | 66.67 |
| 7.5 | 133.33 | 135 | 50.00 |
| 7.5 | 133.33 | 270 | 100.00 |
| 7.5 | 133.33 | 360 | 133.33 |
| 15 | 66.67 | 0 | 0.00 |
| 15 | 66.67 | 45 | 8.33 |
| 15 | 66.67 | 90 | 16.67 |
| 15 | 66.67 | 180 | 33.33 |
| 15 | 66.67 | 135 | 25.00 |
| 15 | 66.67 | 270 | 50.00 |
| 15 | 66.67 | 360 | 66.67 |
| 30 | 33.33 | 0 | 0.00 |
| 30 | 33.33 | 45 | 4.17 |
| 30 | 33.33 | 90 | 8.33 |
| 30 | 33.33 | 180 | 16.67 |
| 30 | 33.33 | 135 | 12.50 |
| 30 | 33.33 | 270 | 25.00 |
| 30 | 33.33 | 360 | 33.33 |
| 60 | 16.67 | 0 | 0.00 |
| 60 | 16.67 | 45 | 2.08 |
| 60 | 16.67 | 90 | 4.17 |
| 60 | 16.67 | 180 | 8.33 |
| 60 | 16.67 | 135 | 6.25 |
| 60 | 16.67 | 270 | 12.50 |
| 60 | 16.67 | 360 | 16.67 |

Figure 8:
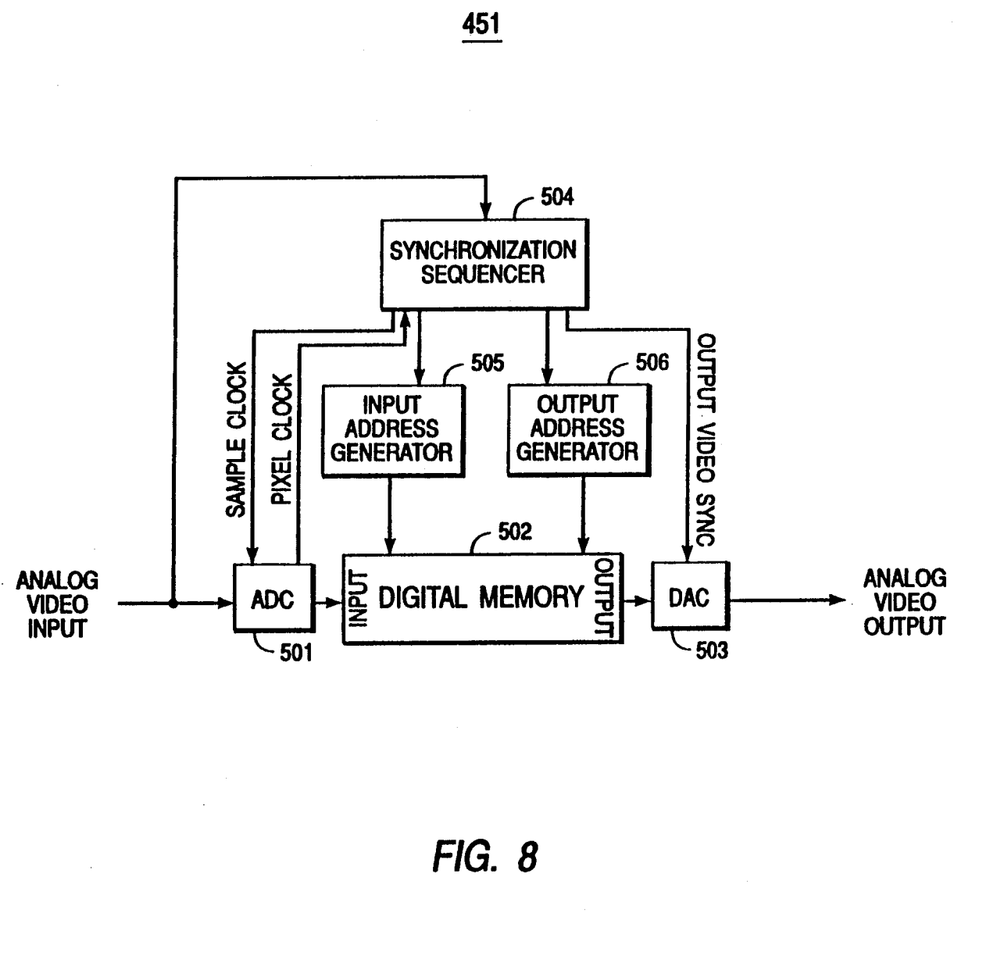
FIG. 8 is a block diagram of a time delay circuit of the present invention.

Referring now to FIG. 8, the construction and operation of time delay circuitry 451 will be described. Time delay circuitry 451 includes an analog-to-digital converter (ADC) 501, a digital memory 502, a digital-to-analog converter (DAC) 503, a synchronization sequencer 504, an input address generator 505, and an output address generator 506. In general, circuitry 451 receives an analog video input signal and then generates an analog video signal which is a time-delayed replication of the input signal.

Synchronization sequencer 504 directs the overall operation of circuitry 451 as follows. Synchronization sequencer 504 receives an input analog video signal having horizontal line synchronizing signals (directing horizontal retraces) and vertical frame synchronizing signals (directing vertical retraces). In response to this input, the sequencer 504 generates a plurality of output signals: a sample clock signal for the ADC 501, time delayed versions of pixel clock and vertical frame synchronizing signals for the output address generator 506, and an output video sync signal for the DAC 503.

Under control of the sample clock signal, the ADC 501 converts the analog video input into a digital video signal, i.e., ADC 501 produces a digital value representation of the moment-to-moment amplitude of the input analog video signal. Typically, sequencer 504 produces a predetermined number (e.g., about 2048) of sample clock pulses during each horizontal line. In response to this series of clock pulses, the ADC 501 produces a corresponding series of digital values (e.g., 10-bit binary values between 0 and 1023) or picture elements ("pixels") representative of the input analog video signal. In addition, the ADC 501 returns a pixel clock signal to the sequencer 504 at the completion of each analog-to-digital conversion, indicating when each pixel value is valid.

The pixel values, in turn, are sent from the ADC 501 to a pixel input port for temporary storage within the digital memory 502. The location in the digital memory 502 where each pixel value is stored is determined from a unique address supplied by the input address generator 505. More particularly, the input address generator 505, under control of the pixel clock, and vertical frame synchronizing signals from the sequencer 504, generates a unique address for each pixel of a given input video image. The address is produced by counting pixel clock pulses, and by resetting the count to zero at each vertical synchronizing signal.

Within the digital memory 502, the pixel values are stored for a predetermined delay time. The delay time is specified as some predetermined number of pixel clock pulses, and is programmable by configuring a settable delay register in the sequencer 504. Thus, a wide variety of delay times are available, and the present invention is not limited to any particular one.

After elapse of the delay time, the pixel values are supplied to the DAC 503 as follows. Under control of the output address generator 506 which receives delayed versions of the pixel clock, and vertical frame synchronizing signals from the sequencer 504, the pixel values are sent to the DAC 503 from an output port of the digital memory 502. The output address generator 506 operates in a manner similar to that of input address generator 505.

From the pixel values, DAC 503 reproduces a time-delayed analog video output signal having an instantaneous or moment-to-moment amplitude corresponding to the time-delayed digital pixel values. According to the output video sync signal, supplied by the sequencer 504, the DAC 503 restores the "horizontal and vertical" synchronizing signals to the digital-to-analog converted video signal. Thus, a time-delayed version of the input analog video signal is recreated at the analog video output.

In a preferred embodiment, delay circuitry 451 includes a modified digital image processor, such as a Video-Optics modified image processor (part no. 932-0830, available from Video-Optics, Inc. of Los Gatos, Calif.). For further documentation of the Video-Optics processor, see IP20 *Modified Image Processor*, manual no. 271-7172 available from Video-Optics, the disclosure of which is hereby incorporated by reference.

Those skilled in the art will appreciate that other time-delay circuitry, such as commercially available digital video time-base correctors, may be employed in place of the circuitry 451. Such a time-base corrector digitizes an input analog video signal and then reproduces it in phase synchrony with a third independently supplied video signal. The third video signal is provided to the time-base corrector via a so-called "GEN-LOCK" input or the like; in a GEN-LOCK input, the horizontal and vertical synchronizations for a video signal are generated so that they are in phase LOCK or synchrony with a separate video sync source. In a particular embodiment, a lateral TV video signal is delayed by the time-base corrector such that the video output signal is phase synchronized with a frontal TV video signal supplied through the GEN-LOCK input.

While the invention is described in some detail with specific reference to a preferred embodiment and certain alternatives, there is no intent to limit the invention to that particular embodiment or those specific alternatives. Those skilled in the art will appreciate other alternatives within the scope of the present invention. Instead of one x-ray controller for both the frontal and lateral x-ray sources, for example, two separate controllers may be employed. Moreover, time delays different from those illustrated may be employed. Therefore, the true scope of the invention is defined not by the foregoing description but by the following claims.

What is claimed is:

1. A single-processor biplane angiographic acquisition system comprising:
   first imaging means for acquiring first video and film images from a first plane at a rate of at least 30 frames per second;
   second imaging means for acquiring second video and film images from a second plane at a rate of at least 30 frames per second;
   means, coupled to said second imaging means, for introducing an acquisition phase difference between acquiring said first video and film images and acquiring said second video and film images;
   a delay circuit, coupled to said second imaging means, to synchronize said video images of said first and second imaging means; and
   a multiplexer, coupled to said first imaging means and to said delay circuit, for alternately selecting one of said first and second video images and directing said selected one video images to a single channel acquisition system at a rate of at least about 30 frames per second.

2. In an angiographic system having a single digital image acquisition processor, a method for providing biplane film and video images, the method comprising the steps of:
   (a) acquiring a first video image and a first film image from a first plane at a first time period;
   (b) acquiring a second video image and a second film image from a second plane at a second time period;
   (c) shifting the second video image by an amount equal to the difference between the first and second time periods;
   (d) combining the first and second video images into a single multiplexed video signal; and
   (e) providing the multiplexed video signal to the single channel image acquisition processor.

3. A biplane cine-film and single channel digital biplane acquisition system, comprising:
   a first and a second imaging subsystem, each subsystem including:
      an x-ray source for producing a plurality of x-rays from a particular direction for striking a subject;
      an image intensifier for receipt of said plurality of x-rays after striking the subject and for producing an image from said received plurality of x-rays;
      a cine-film camera operable at at least about thirty frames per second to record said image on cine-film, said cine-film camera responsive to a control signal to open a shutter and to provide a shutter-open signal when said shutter is open;
      a cine-film camera controller, coupled to said cine-film camera, for producing a shutter signal responsive to said shutter-open signal; and
      a television camera operable at at least about thirty frames per second to record said image as a television image;
   said cine-film camera controller of said first imaging subsystem providing a first slave synch signal to said cine-film controller of said second imaging subsystem to vary a cine-film image acquisition phase between said imaging subsystems to provide said cine-film image acquisition phase between said shutter signals of said cine-film camera controllers, and
   said television controller of said first imaging subsystem providing a second slave synch signal to said television camera of said second imaging subsystem to vary a television image acquisition phase between said imaging subsystems;
   an x-ray controller, coupled to said cine-film controllers and to said x-ray sources, for activating said x-ray source of a particular one of said first and second imaging subsystems in response to an assertion of said shutter signal of said cine-film camera controller of said particular one imaging subsystem;
   a delay circuit, coupled to an output of said television camera of said second imaging subsystem, for removing said television image acquisition delay to produce a second imaging subsystem television camera image signal synchronized with a first imaging subsystem television camera image signal; and
   a multiplexer, coupled to said first imaging subsystem television camera and to said delay circuit, for alternately selecting one of said television imaging signals to direct to a single channel acquisition system.

4. A method for operating a biplane image acquisition system using video and cine-film images for both first and second views of a subject, comprising the steps of:
   operating alternately at a rate of at least about thirty frames per second a first and second imaging subsystem, each imaging subsystem including:

an x-ray source for producing a plurality of x-rays from a particular direction for striking the subject;

an image intensifier for receipt of said plurality of x-rays after striking said subject and for producing an image from said receiving plurality of x-rays;

a cine-film camera operable at at least about thirty frames per second to record said image on cine-film, said cine-film camera responsive to a control signal to open a shutter and to provide a shutter-open signal when said shutter is open;

a cine-film camera controller, coupled to said cine-film camera, for producing a shutter signal responsive to said shutter-open signal; and a television camera operable at at least about thirty frames per second to record said image as a television image;

said cine-film camera controller of said first imaging subsystem providing a first slave synch signal to said cine-film controller of said second imaging subsystem to vary a cine-film image acquisition phase between said imaging subsystems to provide said cine-film image acquisition phase between said shutter signals of said cine-film camera controllers, and said television controller of said first imaging subsystem providing a second slave synch signal to said television camera of said second imaging subsystem to vary a television image acquisition phase between said imaging subsystems;

delaying said television image from said second imaging subsystem to synchronize said television images from said imaging subsystems; and multiplexing said synchronized television images into a single channel acquisition channel.

5. A biplane acquisition system, comprising:

a first and a second imaging subsystem, each including:

an x-ray source for producing a plurality of x-rays from a particular direction for striking a subject;

an image intensifier for receipt of said plurality of x-rays after striking said subject and for producing an image from said received plurality of x-rays;

a film camera operable at at least about thirty frames per second to record said image on cine-film, said cine-film camera responsive to a control signal to open a shutter and to provide a shutter-open signal when said shutter is open;

a film camera controller, coupled to said cine-film camera, for producing a shutter signal responsive to said shutter-open signal; and a television camera operable at at least about 30 frames per second to record said image as a television image, and;

means, coupled to said imaging subsystems, for varying an acquisition phase between said television images;

a delay, coupled to said second imaging subsystem, for removing said acquisition phase from said second television image to resynchronize said television images; and a multiplexer, coupled to said imaging subsystems, for alternately selecting said television images and directing them to a single channel acquisition system.

* * * * *